United States Patent
Yu et al.

(10) Patent No.: US 7,129,034 B2
(45) Date of Patent: Oct. 31, 2006

(54) DIFFERENTIATION OF WHOLE BONE MARROW

(75) Inventors: John S. Yu, Los Angeles, CA (US); Peter Kabos, Los Angeles, CA (US); Moneeb Ehtesham, Nashville, TN (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 472 days.

(21) Appl. No.: 10/253,759

(22) Filed: Sep. 24, 2002

(65) Prior Publication Data

US 2003/0082160 A1   May 1, 2003

Related U.S. Application Data

(60) Provisional application No. 60/334,957, filed on Oct. 25, 2001.

(51) Int. Cl.
| | |
|---|---|
| *C12N 5/00* | (2006.01) |
| *C12N 5/06* | (2006.01) |
| *C12N 5/08* | (2006.01) |
| *C12N 5/10* | (2006.01) |

(52) U.S. Cl. .................. 435/1.1; 435/377; 435/372; 435/325; 435/368

(58) Field of Classification Search ................ 435/325, 435/350, 351, 352, 353, 354, 355, 363, 366, 435/368, 372
See application file for complete search history.

(56) References Cited

U.S. PATENT DOCUMENTS

| | | | |
|---|---|---|---|
| 4,714,680 A | 12/1987 | Civin | |
| 4,965,204 A | 10/1990 | Civin | |
| 5,035,994 A | 7/1991 | Civin | |
| 5,130,144 A | 7/1992 | Civin | |
| 5,166,065 A | 11/1992 | Williams et al. | |
| 5,429,938 A | 7/1995 | Humes | |
| 5,436,151 A | 7/1995 | McGlave et al. | |
| 5,437,994 A | 8/1995 | Emerson et al. | |
| 5,449,620 A | 9/1995 | Khillan | |
| 5,556,783 A | 9/1996 | Lavker et al. | |
| 5,589,376 A | 12/1996 | Anderson et al. | |
| 5,643,741 A | 7/1997 | Tsukamoto et al. | |
| 5,646,043 A | 7/1997 | Emerson et al. | |
| 5,654,183 A | 8/1997 | Anderson et al. | |
| 5,665,557 A | 9/1997 | Murray et al. | |
| 5,670,351 A | 9/1997 | Emerson et al. | |
| 5,672,499 A | 9/1997 | Anderson et al. | |
| 5,677,136 A | 10/1997 | Simmons et al. | |
| 5,681,559 A | 10/1997 | DiGiusto et al. | |
| 5,693,482 A | 12/1997 | Anderson et al. | |
| 5,728,581 A | 3/1998 | Schwartz et al. | |
| 5,753,506 A | 5/1998 | Johe | |
| 5,772,994 A | 6/1998 | Ildstad et al. | |
| 5,806,529 A | 9/1998 | Reisner et al. | |
| 5,817,773 A * | 10/1998 | Wilson et al. ............... | 530/399 |
| 5,824,489 A | 10/1998 | Anderson et al. | |
| 5,849,553 A | 12/1998 | Anderson et al. | |
| 5,851,832 A | 12/1998 | Reynolds et al. | |
| 5,912,133 A | 6/1999 | Lemischka | |
| 5,928,947 A | 7/1999 | Anderson et al. | |
| 5,965,436 A | 10/1999 | Thiede et al. | |
| 5,968,829 A | 10/1999 | Carpenter | |
| 6,013,521 A * | 1/2000 | Gage et al. ............... | 435/368 |
| 6,204,053 B1 | 3/2001 | Dinsmore | |
| 6,528,245 B1 * | 3/2003 | Sanchez-Ramos et al. ... | 435/1.1 |
| 6,833,269 B1 * | 12/2004 | Carpenter ................... | 435/377 |
| 2002/0045261 A1 | 4/2002 | Snyder et al. | |
| 2002/0115213 A1 | 8/2002 | Snyder et al. | |
| 2005/0074435 A1 * | 4/2005 | Casper et al. .............. | 424/93.7 |

FOREIGN PATENT DOCUMENTS

| | | |
|---|---|---|
| EP | 0695351 | 8/1999 |
| WO | 00/66713 | 11/2000 |
| WO | 01/66698 | 9/2001 |
| WO | 01/68148 | 9/2001 |

OTHER PUBLICATIONS

Gage et al. (1995) "Isolation, characterization, and use of stem cells from the CNS," Annu Rev Neurosci. 18: 159-92.*
Bikfalvi et al. (1997) "Biological Roles of Fibroblast Growth Factor-2" Endocrine Reviews 18(1): 26-45.*
Svendsen et al. (Dec. 1, 1998) "A new method for rapid and long term growth of human neural precursor cells" Journal of Neuroscience Methods 85(2): 141-152.*
Tropepe et al., Developmental Biology 208: 166-188.*
U. Englund et al., "Site-Specific Neuronal Differentiation of Growth Factor Expanded Human Neural Progenitor Cells After Transplantation to the Neonatal Rat Brain," *Society for Neuroscience Abstracts*, vol. 25, No. 1/2, p. 213 (1999).

(Continued)

*Primary Examiner*—David S. Romeo
*Assistant Examiner*—Daniel C. Gamett
(74) *Attorney, Agent, or Firm*—Seth D. Levy; Davis Wright Tremaine LLP

(57) ABSTRACT

A method is described for generating a clinically significant volume of neural progenitor cells from whole bone marrow. A mass of bone marrow cells may be grown in a culture supplemented with fibroblast growth factor-2 (FGF-2) and epidermal growth factor (EGF). Further methods of the present invention are directed to utilizing the neural progenitor cells cultured in this fashion in the treatment of various neuropathological conditions, and in targeting delivery of cells transfected with a particular gene to diseased or damaged tissue.

13 Claims, 15 Drawing Sheets
(14 of 15 Drawing Sheet(s) Filed in Color)

OTHER PUBLICATIONS

H.G. Kuhn et al., "Epidermal Growth Factor and Fibroblast Growth Factor-2 have Different Effects on Neural Progenitors in the Adult Rat Brain," *J. Neuroscience*, vol. 17, No. 15, pp. 5820-5829 (1997).

F.H. Gage, "Mammalian Neural Stem Cells," *Science*, vol. 287, No. 5457, pp. 1433-1438 (2000).

D.J. Martens et al., "In Vivo Infusions of Exogenous Growth Factors into the Fourth Ventricle of the Adult Mouse Brain Increase the Proliferation of Neural Progenitors Around the Fourth Ventricle and the Central Canal of the Spinal Cord," European J. Neuroscience, vol. 16, No. 6, pp. 1045-1057 (2002).

D. W. Pincus et al., "Fibroblast Growth Factor—2/Brain-Derived Neurotrophic Factor-Associated Maturation of New Neurons Generated from Adult Human Subependymal Cells," *Annals of Neurology*, vol. 43, No. 5, pp. 576-585 (May 1998).

C. B. Johansson et al., "Rapid Communication—Neural Stem Cells in the Adult Human Brain," *Experimental Cell Research*, vol. 253, pp. 733-736 (1999).

S. F. Pagano et al., "Isolation and Characterization of Neural Stem Cells from the Adult Human Olfactory Bulb," *Stem Cells 2000*, vol. 18, pp. 295-300 (2000).

U. Lendahl et al., "CNS Stem Cells Express a New Class of Intermediate Filament Protein," *Cell*, vol. 60, No. 4, pp. 585-595 (Feb. 1990).

J. G. Toma et al., "Isolation of multipotent adult stem cells from the dermis of mammalian skin," *Nature Cell Biology*, vol. 3, pp. 778-784 (2001).

E. Mezey et al., "Turning Blood into Brain: Cells Bearing Neuronal Antigens Generated in Vivo from Bone Marrow," *Science*, vol. 290, pp. 1779-1782 (Dec. 2000).

T. R. Brazelton et al., "From Marrow to Brain: Expression of Neuronal Phenotypes in Adult Mice," *Science*, vol. 290, pp. 1775-1779 (Dec. 2000).

M. A. Eglitis and E. Mezey, "Hematopoietic cells differentiate into both microglia and macroglia in the brains of adult mice," *Proc. National Academy of Science USA/Neurobiology*, vol. 94, pp. 4080-4085 (Apr. 1997).

D. Woodbury et al., "Adult Rat and Human Bone Marrow Stromal Cells Differentiate into Neurons," *Journal of Neuroscience Research*, vol. 61, pp. 364-370 (2000).

J. Sancehz-Ramos et al., "Adult Bone Marrow Stromal Cells Differentiate into Neural Cells *in Vitro*," *Experimental Neurology*, vol. 164, pp. 247-256 (2000).

Vogel, Gretchen; "Can Old Cells Learn New Tricks," *The American Association for the Advancement of Science*, vol. 287, No. 5457, pp. 1418-1419 (Feb. 25, 2000).

Vogel, Gretchen; "Capturing the Promise of Youth," *The American Association for the Advancement of Science*, vol. 286, No. 5448, pp. 2238-2239 (Dec. 17, 1999).

Weissman, Irving L.; "Translating Stem and Progenitor Cell Biology to the Clinic: Barriers and Opportunities," *The American Association for the Advancement of Science*, vol. 287, No. 5457, pp. 1442-1446 (Feb. 25, 2000).

Barinaga, Marcia; "Fetal Neuron Grafts Pave the Way for Stem Cell Therapies," *The American Association for the Advancement of Science*, vol. 287, No. 5457, pp. 1421-1422 (Feb. 25, 2000).

Sanchez-Ramos, J., "Adult Bone Marrow Stromal Cells Differentiate Into Neural Cells in Vitro", Experimental Neurology, 164:247-256 (2000).

Woodbury, D., "Adult Rat and Human Bone Marrow Stromal Cells Differentiate Into Neurons", Journal of Neuroscience Research 61:364-370 (2000).

Mezey, E., "Turning Blood into Brain: Cells Bearing Neuronal Antigens Generated in vivo from Bone Marrow", Science 290:1779-1782 (Dec. 2000).

Jiang, Y., "Pluripotency of Mesenchymal Stem Cells Derived From Adult Marrow", Nature, 418:41-49 (Jul. 2002).

* cited by examiner

A

B

C

D

F
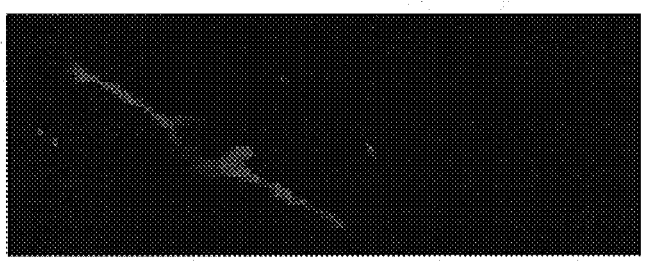
Figure 4
G
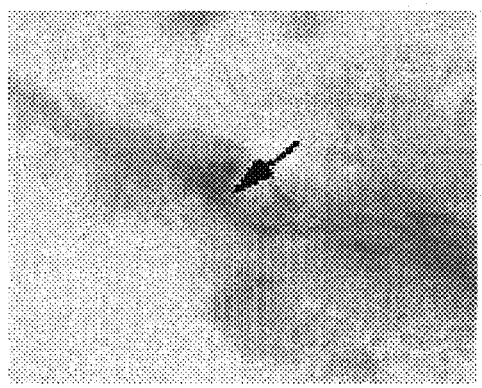
H
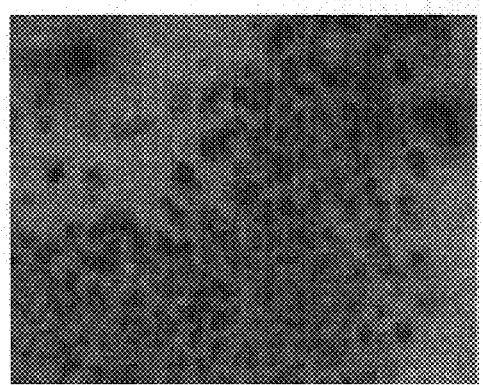

A

B

DIFFERENTIATION OF WHOLE BONE MARROW

This application claims the benefit of priority under 35 U.S.C. § 119(e) of provisional application Ser. No. 60/334,957, filed Oct. 25, 2001, the contents of which are hereby incorporated by reference.

FIELD OF THE INVENTION

Embodiments of the present invention are directed to a method for generating a clinically substantial volume of neural progenitor cells from mammalian whole bone marrow. Further embodiments of the present invention are directed to the treatment of neurological disorders using neural progenitor cells cultured in this fashion.

BACKGROUND OF THE INVENTION

Nearly every cell in an animal's body, from neural to blood to bone, owes its existence to a stem cell. A stem cell is commonly defined as a cell that (i) is capable of renewing itself; and (ii) can give rise to more than one type of cell (that is, a differentiated cell) through asymmetric cell division. F. M. Watt and B. L. M. Hogan, "Out of Eden: Stem Cells and Their Niches," *Science*, 284, 1427–1430 (2000). Stem cells give rise to a type of stem cell called progenitor cells; progenitor cells, in turn, proliferate into the differentiated cells that populate the body.

The prior art describes the development, from stem cell to differentiated cells, of various tissues throughout the body. U.S. Pat. No. 5,811,301, for example, the disclosure of which is hereby incorporated by reference, describes the process of hematopoiesis, the development of the various cells that comprise blood. The process begins with what may be a pluripotent stem cell, a cell that can give rise to every cell of an organism (there is only one cell that exhibits greater developmental plasticity than a pluripotent stem cell; this is a fertilized ovum, a single, totipotent stem cell that can give rise to an entire organism when implanted into the uterus). The pluripotent stem cell gives rise to a myeloid stem cell. Certain maturation-promoting polypeptides cause the myeloid stem cell to differentiate into precursor cells, which in turn differentiate into various progenitor cells. It is the progenitor cells that proliferate into the various lymphocytes, neutrophils, macrophages, and other cells that comprise blood tissue of the body.

This description of hematopoiesis is vastly incomplete, of course: biology has yet to determine a complete lineage for all the cells of the blood (e.g., it is has yet to identify all the precursor cells between the myeloid stem cell and the progenitor cells to which it gives rise), and it has yet to determine precisely how or why the myeloid cell differentiates into progenitor cells. Even so, hematopoiesis is particularly well studied; even less is known of the development of other organ systems. With respect to the brain and its development, for example, U.S. Pat. No. 6,040,180, the disclosure of which is hereby incorporated by reference, describes the "current lack of understanding of histogenesis during brain development." U.S. Pat. No. 5,849,553, the disclosure of which is hereby also incorporated by reference, describes the "uncertainty in the art concerning the development potential of neural crest cells."

The identification and isolation of stem cells has daunted researchers for decades. To date, no one has identified an individual neural stem cell or hematopoietic stem cell. F. H. Gage, "Mammalian Neural Stem Cells," *Science*, 287, 1433–1488 (2000). There are two principal difficulties. First, stem cells are rare. In bone marrow, for example, where hematopoiesis occurs, there is only one stem cell for every several billion bone marrow cells. G. Vogel, "Can Old Cells Learn New Tricks?" *Science*, 287, 1418–1419 (2000). Second, and more importantly, researchers have been unable to identify molecular markers which are unique to stem cells; to the typical immunoassay, most stem cells look like any other cell. Id. Compounding this problem is that primitive stem cells may be in a quiescent state. As a result, they may express few molecular markers. F. H. Gage, supra.

A method to effectively isolate stem cells and culture them in clinically significant quantities would be of immense importance. Researchers are already transplanting immature neurons, presumed to contain neural stem cells, from human fetuses to adult patients with neurodegenerative disease. The procedure has reduced symptoms by up to 50% in patients with Parkinson's disease in one study. M. Barinaga, "Fetal Neuron Grafts Pave the Way for Stem Cell Therapies," *Science*, 287, 1421–1422 (2000). Many of the shortcomings of this procedure, including the ethical and practical difficulties of using material derived from fetuses and the inherent complications of harvesting material from adult brain tissue, could be addressed by using cultures of isolated stem cells, or stem cells obtained from adult individuals. D. W. Pincus et al., *Ann. Neurol.* 43:576–585 (1998); C. B. Johansson et al., *Exp. Cell. Res.* 253:733–736 (1999); and S. F. Pagano et al., *Stem Cells* 18:295–300 (2000). However, the efficient and large-scale generation of neural progenitor cells for use in the treatment of neurological disorders has been a challenge.

Recent evidence has suggested that progenitor cells outside the central nervous system and bone marrow cells in paricular may have the ability to generate either neurons or glia in vivo. J. G. Toma et al., *Nat. Cell Biol.* 3:778–783 (2001); E. Mezey et al., *Science* 290:1779–1782 (2000); T. R. Brazleton et al., *Science* 290:1775–1779 (2000); and M. A. Eglitis et al., *Proc Natl. Acad. Sci.* 94:4080–4085 (1997). Bone marrow stromal cells have also been shown to be capable of differentiating into neurons and glia in vitro after a complicated and time-consuming culture process spanning several weeks. The generation of neural progenitor cells from whole bone marrow has, however, not been reported.

SUMMARY OF THE INVENTION

The invention described herein provides an efficient method of generating a clinically significant quantity of neural progenitor cells. These neural progenitor cells may be generated from bone marrow or other appropriate sources, and may be used to treat a variety of conditions, particularly neuropathological conditions. Owing to the neural progenitor cells' ability to track diseased or damaged neural tissue and to further replace the lost function of such tissue, the cells of the present invention are particularly useful in the treatment of conditions wherein neural tissue itself is damaged.

Still further embodiments of the present invention describe the use of the neural progenitor cells to target the delivery of various compounds to damaged or diseased neural tissue. Neural progenitor cells may be caused to carry a gene that induces the cells themselves to secrete such compounds, or to otherwise effect the local production of such compounds by, for example, initiating or promoting a particular biochemical pathway. Since the neural progenitor cells that carry these genes may track diseased or damaged neural tissue, delivery of the particular compound may be correspondingly targeted to such tissue. A dual treatment effect is accomplished when the neural progenitor cells both replace lost or damaged neural tissue function while simultaneously effecting the targeted delivery of a therapeutic compound.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

FIG. 1A depicts cells from whole bone marrow that, when plated on poly-D-lysine, form a monolayer that gives rise to distinct cellular spheres after four days in culture. FIG. 1B depicts the spheres of FIG. 1A at higher magnification; cells may be easily collected, subcultured, and propagated separately in the presence of growth factors. FIG. 1C depicts that the spheres, once differentiated, attach and cells start migrating outward (arrows indicate migrating cells). FIG. 1D depicts that the formed spheres detach from the bottom and afterwards remain free-floating.

FIGS. 2A and 2B indicate that neurospheres (i.e., spheres derived from neural cells) and bone marrow-derived spheres, respectively, were morphologically indistinguishable. FIGS. 2C and 2D indicate that the pattern of nestin expression (red) was similar both in neurospheres and bone marrow derived spheres, respectively. Nuclei of cells appear blue owing to being counterstained with 4',6-diamidino-2-phenylindole (DAPI).

FIG. 3A indicates that the bone marrow-derived spheres expressed the ectodermal marker vimentin. As depicted in FIG. 3B, a weak staining for fibronectin was also observed in the neural progenitor cells. As depicted in FIG. 3C, bone marrow-derived spheres exhibit strong expression of CD90, and, as depicted in FIG. 3D, the majority of the cells in spheres exhibit nuclear expression of Neurogenin 1.

FIGS. 4B and 4C depict neural progenitor cells of the present invention expressing the glial cell marker glial fibrillary acidic protein (GFAP) after eight and nine days of differentiation, respectively (cellular nuclei counterstained with DAPI). FIGS. 4D and 4E depict neural progenitor cells of the present invention expressing the neuronal marker Neuron Specific Enolase (NSE) after eight days of differentiation (cellular nuclei counterstained with DAPI). Scattered cells also expressed the later neuronal marker MAP2, as depicted in FIG. 4F. After transplantation of the bone marrow derived spheres into the hippocampus of a syngeneic animal, cells expressing NeuN were found, as depicted in FIG. 4G. Some of these cells appeared to integrate into the hippocampal structure, as depicted in FIG. 4H. FIGS. 4I, 4J and 4K depict a similar differentiation of bone marrow derived cells, with alternate antibodies used for immunocytochemistry. FIG. 4I depicts the use of the oligodendrocyte marker CNPase (1:400 Sigma) at 40× magnification, while FIGS. 4J and 4K depict the use of the neuronal marker NF200 (1:100 Chemicon) at 20× and 40× magnification, respectively.

FIG. 7A depicts neural progenitor cells grown into spherical aggregates. FIG. 7B depicts nestin expression by these neurospheres (nuclei counterstained with DAPI). Neurons expressed β-III tubulin, astrocytes expressed GFAP, and oligodendrocytes expressed CNPase (FIGS. 7C, 7D, and 7E, respectively). FIG. 7F depicts expression of β-galactosidase by neural progenitor cells infected in vitro with AdLacZ. Magnification 400× for FIGS. 7B, 7C, 7D, and 7E; 100× for FIGS. 7A and 7F.

FIG. 9A depicts a thin outgrowth of tumor cells deep into adjacent normal brain. FIG. 9B depicts a direct extension of tumor mass into adjacent tissue. FIG. 9C depicts a migration of glioma cells away from the primary tumor bed along a white matter tract. FIG. 9D depicts a tumor microsatellite independent of a main tumor mass. FIG. 9E depicts a high power photomicrograph of the microsatellite depicted in FIG. 9D; further depicting β-galactosidase-positive neural progenitor cells interspersed with tumor cells. FIG. 9F shows an inoculation of neural progenitor cells (left panel) and a tumor mass (right panel) into which neural progenitor cells migrated from the opposite hemisphere (inset box). Neural progenitor cells appear blue (expressing β-galactosidase), whereas tumor cells appear red (hypercellular areas stained intensively with neural red). "T" represents tumor mass, outgrowths, and microsatellites. Arrows indicate disseminating neural progenitor cells closely following migrating pockets of tumor.

FIG. 10A depicts a flow cytometry analysis demonstrating intratumoral T-cell infiltration in brain tissue treated with neural progenitor cells secreting IL-12 (left panel) and 3T3-IL-12 (center panel), and a comparative lack of infiltration in tissue treated with neural progenitor cells secreting LacZ (right panel). CD4+ (left panel) and CD8+ (right panel) intratumoral infiltration is depicted in tissue treated with neural progenitor cells secreting 3T3-IL-12, LacZ, and IL-12 (FIGS. 10B, 10C, and 10D, respectively). Aggregates appeared along the tumor/normal tissue boundary in tissue treated with neural progenitor cells secreting IL-12 (FIG. 10D, arrows indicate aggregates). FIG. 10E depicts a comparison of T-cell infiltration in comparable outgrowths from a primary tumor bed for tissue treated with neural progenitor cells secreting IL-12 and 3Y3-IL-12 (FIGS. 10E, left and right panels, respectively). "T" designates tumor and "N" designates normal brain tissue. Magnification 100× for FIGS. 10B, 10C, and 10D, and 200× for FIG. 10E.

FIG. 11A depicts a migration of transplanted cells (green). FIG. 11B depicts individual cells expressing NSE (red) and GFP together with NSE (yellow). Transplanted cells were stained for NSE and exhibit GFP (green), NSE (red), and the merged image of green fluorescent protein (GFP) and NSE (green and red) (FIGS. 11C, 11D, and 11E, respectively). Magnification 100× for FIG. 11A; 630× for FIG. 11B; and 200× for FIGS. 11C, 11D, and 11E.

DETAILED DESCRIPTION OF THE INVENTION

Figure 1:
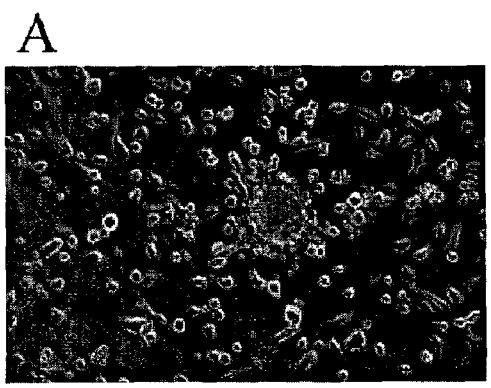
FIG. 1 depicts neural progenitor cells obtained from human bone marrow in accordance with an embodiment of the present invention.
Figure 1:
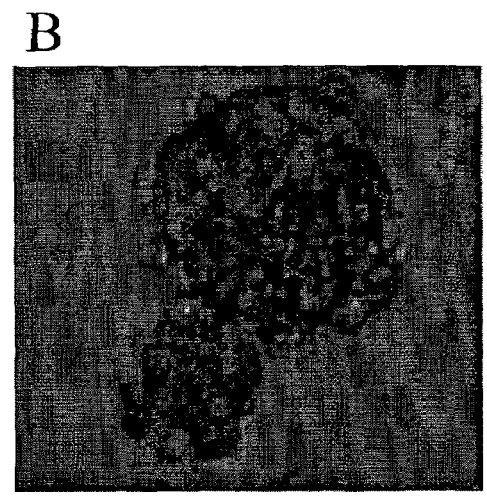
Figure 1:
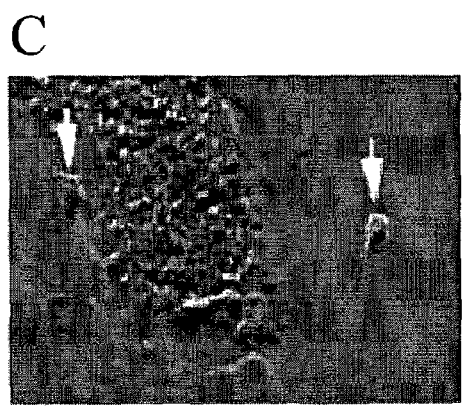
Figure 1:
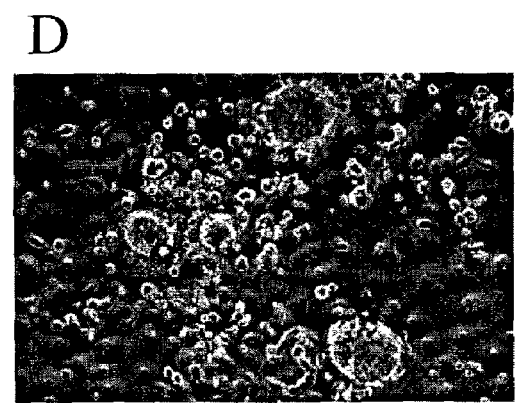

Methods of the present invention are based on adult bone marrow as a viable alternative source of neural progenitor cells that may be used in therapeutic strategies for a variety of neuropathological conditions.

Any population of cells where neural progenitor cells are suspected of being found may be used in accordance with the method of the present invention. Such populations of cells may include, by way of example, mammalian bone marrow, brain tissue, or any suitable fetal tissue. Preferably, cells are obtained from the bone marrow of a non-fetal mammal, and most preferably from a human. U.S. Pat. Nos. 6,204,053 B1 and 5,824,489, the disclosures of which are hereby incorporated by reference, identify additional sources of cells that contain or are thought to contain stem cells; any of these cells may be used in accordance with the methods of the present invention.

In one embodiment of the present invention, a mass of cells may be harvested or otherwise obtained from an appropriate source, such as, by way of example, adult human bone marrow. The mass of cells may thereafter be grown in a culture, and may be further subcultured where desirable, to generate further masses of cells. Any appropriate culture medium may be used in accordance with the methods of the present invention, such as, by way of example, serum-free Dulbecco's modified Eagle medium (DMEM)/F-12 medium.

The medium of the present invention may include various medium supplements, growth factors, antibiotics, and additional compounds. Supplements may illustratively include B27 supplement and/or N2 supplement (both available from Invitrogen Corporation); growth factors may illustratively include fibroblast growth factor-2 (FGF-2), epidermal growth factor (EGF), and/or leukemia inhibitory factor (LIF); and antibiotics may illustratively include penicillin and/or streptomycin. In preferred embodiments of the present invention, growth factors are included in an amount of from about 15 ng/ml to about 25 ng/ml. Additional compounds suitable for use in the present invention may include, but are in no way limited to, interleukin-3 (IL-3), stem cell factor-1 (SCF-1), sonic hedgehog (Shh), and fms-like tyrosine kinase-3 (Flt3) ligand. While not wishing to be bound by any theory, it is believed that these particular compounds may enhance the production of spheres in accordance with the methods of the present invention. Additional or substituted supplements, growth factors, antibiotics, and additional compounds suitable for use with the methods of the present invention may be readily recognized by one of skill in the art, and these are contemplated as being within the scope of the present invention. In a most preferred embodiment of the present invention, a culture medium is DMEM/F-12 medium supplemented with B27, and additionally includes 10 ng/ml of both FGF-2 and EGF, as well as penicillin and streptomycin.

After a sufficient time period (generally from about three to about six days), clusters of neural progenitor cells (e.g., spheres) may form in a culture medium in which stem cells obtained as described above are included. Individual clusters of neural progenitor cells may be removed from the medium and sub-cultured separate from one another. Such separation may be repeated any desirable number of times to generate a clinically significant volume of neural progenitor cells. These neural progenitor cells may be capable of differentiating into a variety of neural cells, such as, astrocytes, neurons, and oligodendroglia.

As used herein, a "clinically significant volume" is an amount of cells sufficient to utilize in a therapeutic treatment of a disease condition, including a neuropathological condition. Furthermore, as used herein, "treatment" includes, but is not limited to, ameliorating a disease, lessening the severity of its complications, preventing it from manifesting, preventing it from recurring, merely preventing it from worsening, mitigating an undesirable biologic response (e.g., inflammation) included therein, or a therapeutic effort to effect any of the aforementioned, even if such therapeutic effort is ultimately unsuccessful.

The neural progenitor cells of the present invention possess a host of potential clinical and therapeutic applications, as well as applications in medical research. Two possible therapeutic mechanisms include: (1) using the cells as a delivery vehicle for gene products by taking advantage of their ability to migrate after transplantation, and (2) using the cells to replace damaged or absent neural tissue, thereby restoring or enhancing tissue function.

As discussed in the ensuing Examples, and with reference to the first therapeutic mechanism indicated above, the neural progenitor cells of the present invention are capable of "tracking" diseased or damaged tissue in vivo. The cells may therefore be used to aid in the targeted delivery of various compounds useful in the treatment of diseased or damaged tissue. Delivery of such compounds may be accomplished by transfecting the cells with a gene that induces the cell to, for example, constitutively secrete that compound itself, or promote a biochemical pathway that effects a local production of that compound.

Thus, in one embodiment of the present invention, neural progenitor cells may be transfected with or otherwise caused to carry a particular gene, as per any conventional methodology. Such methodologies may include introducing a particular gene into the neural progenitor cells as a plasmid, or, more preferably, using somatic cell gene transfer to transfect the cells utilizing viral vectors containing appropriate gene sequences. Suitable viral vectors may include, but are in no way limited to, expression vectors based on recombinant adenoviruses, adeno-associated viruses, retroviruses or lentiviruses, although non-viral vectors may alternatively be used. In a preferred embodiment of the present invention, one employs adenovirus serotype 5 ("Ad5")-based vectors (available from Quantum Biotechnology, Inc., Montreal, Quebec, Canada) to deliver and express desirable gene sequences in the neural progenitor cells of the present invention. Once caused to carry the desired gene, the neural progenitor cells may be implanted in or otherwise administered to a mammal.

By employing this therapeutic mechanism, the neural progenitor cells of the present invention may be used to treat a variety of pathological conditions; potentially any condition where mammalian neural tissue is diseased or damaged to the point that neural progenitor cells will track the same. In the area of neuropathological disorders, this therapeutic modality may be used in the treatment of numerous conditions, some examples of which may include: brain tumors (e.g., by targeting the delivery of cytokines or other agents that enhance the immune response, or by targeting the delivery of compounds that are otherwise toxic to tumor cells); brain ischemia (e.g., by targeting the delivery of neuroprotective substances such as brain-derived neurotrophic factor (BDNF), nerve growth factor (NGF), and neurotrophin-3, -4, and -5 (NT-3, NT-4, NT-5)); spinal cord injury (e.g., again, by targeting the delivery of neuroprotective substances, or by targeting the delivery of substances inducing neurite growth such as basic fibroblast growth factor (bFGF), insulin-like growth factor-1 (IGF-1), and glial-derived neurotrophic factor (GDNF)); and neurodegenerative disorders, such as Alzheimer's or Parkinson's Disease (e.g., again, by targeting the delivery of neuroprotective substances or growth factors, or by targeting the delivery of other neuroprotective factors such as amyloid precursor proteins or protease nexin-1).

As discussed in the ensuing Examples, and with reference to the second therapeutic mechanism indicated above, the neural progenitor cells of the present invention are also able to replace neurons and glia in vivo. The cells may therefore be used to replace diseased or damaged neural tissue, and, owing to the cells' additional capacity to track diseased or damaged tissue in vivo, once administered, the cells may configure themselves to an appropriate physiological site to effect this therapeutic mechanism.

Given the ability of the neural progenitor cells of the present invention to replace lost or damaged neural tissue function, these cells may be useful in the treatment of numerous neuropathological conditions, many of which are similar to those enumerated above. By way of example, even in a state where the cells have not been transfected or otherwise caused to carry a particular gene, the cells may be used in the treatment of brain tumors, brain ischemia, spinal cord injury, and various neurodegenerative disorders.

Neural progenitor cells that are, in fact, transfected or otherwise caused to carry a desirable gene may also provide the additional neural cell function replacement capacity discussed in this mechanism; thereby imparting a dual treatment effect to the recipient. The dual treatment effect may include the replacement of lost or damaged cell function (e.g., as per the second therapeutic mechanism) in conjunction with the targeted delivery of a beneficial compound to that same region (e.g., as per the first therapeutic mechanism). Therefore, in the illustrative instance of brain tumor treatment, the neural progenitor cells may be transfected with a gene that induces the secretion of cytokines (e.g., tumor necrosis factor (TNF) or interleukin-1 (IL-1)), and implanted or otherwise administered to the brain of a recipient. Once administered, the cells may track the tissue damaged by the tumor, replacing at least a portion of the lost brain function, while simultaneously secreting cytokines that may induce an immune response against the tumor cells. This dual treatment effect is further described in the ensuing Examples.

Neural progenitor cells developed through culture as described above may be implanted in or otherwise administered to a mammal to effect the therapeutic mechanisms previously discussed. Once implanted or otherwise administered, these cells may relocate to an area of diseased tissue, such as, but not limited to, brain tumors, tissue damaged by stroke or other neurodegenerative disease, and the like. Moreover, the neural progenitor cells may multiply in vivo, and may further follow diseased tissue as it spreads (e.g., as a tumor spreads). Implantation may be performed by any suitable method as will be readily ascertained without undue experimentation by one of ordinary skill in the art, such as injection, inoculation, infusion, direct surgical delivery, or any combination thereof.

EXAMPLES

All references cited herein are hereby incorporated by reference in their entirety. The following examples are typical of the procedures that may be used to culture neural progenitor cells according to a method of the present invention. Further examples are typical of the procedures that may be used to perform gene transfer into these cells and/or implant these cells into a patient to treat a neurological disorder in accordance with another embodiment of the present invention. Modifications of these examples will be apparent to those skilled in the art.

Example 1

Isolation and Preparation of Neural Progenitor Cells

Whole bone marrow was harvested from the femurs of adult Fisher rats between 16 and 24 weeks of age. Cultures were plated on poly-D-lysine coated 24 well plates at a density of 106 cells per well. The cells were cultured in serum-free Dulbecco's modified Eagle medium (DMEM)/F-12 medium supplemented with B27 (obtained from Gibco BRL; Gaithersburg, Md.), 20 ng/ml FGF-2 and 20 ng/ml EGF (both available from Sigma Chemical Co.; St. Louis, Mo.; hereinafter "Sigma"), along with penicillin and streptomycin (both available from Omega Scientific, Inc.; Tarzana, Calif.).

After four days in culture, numerous floating spheres of between about 10 to about 100 cells were distinctly visible separate from an underlying adherent monolayer (FIG. 1A). These spheres were collected and sub-cultured separately (FIG. 1B). The cellular aggregates continued to expand and the rate of proliferation remained stable even after multiple disassociations and passages. Numerous cells in these spheres tested positive for nestin (FIGS. 2C and 2D), a known marker for neural stem cells. U. Lendahl et al., *Cell* 60:585–595 (1990).

Figure 4:
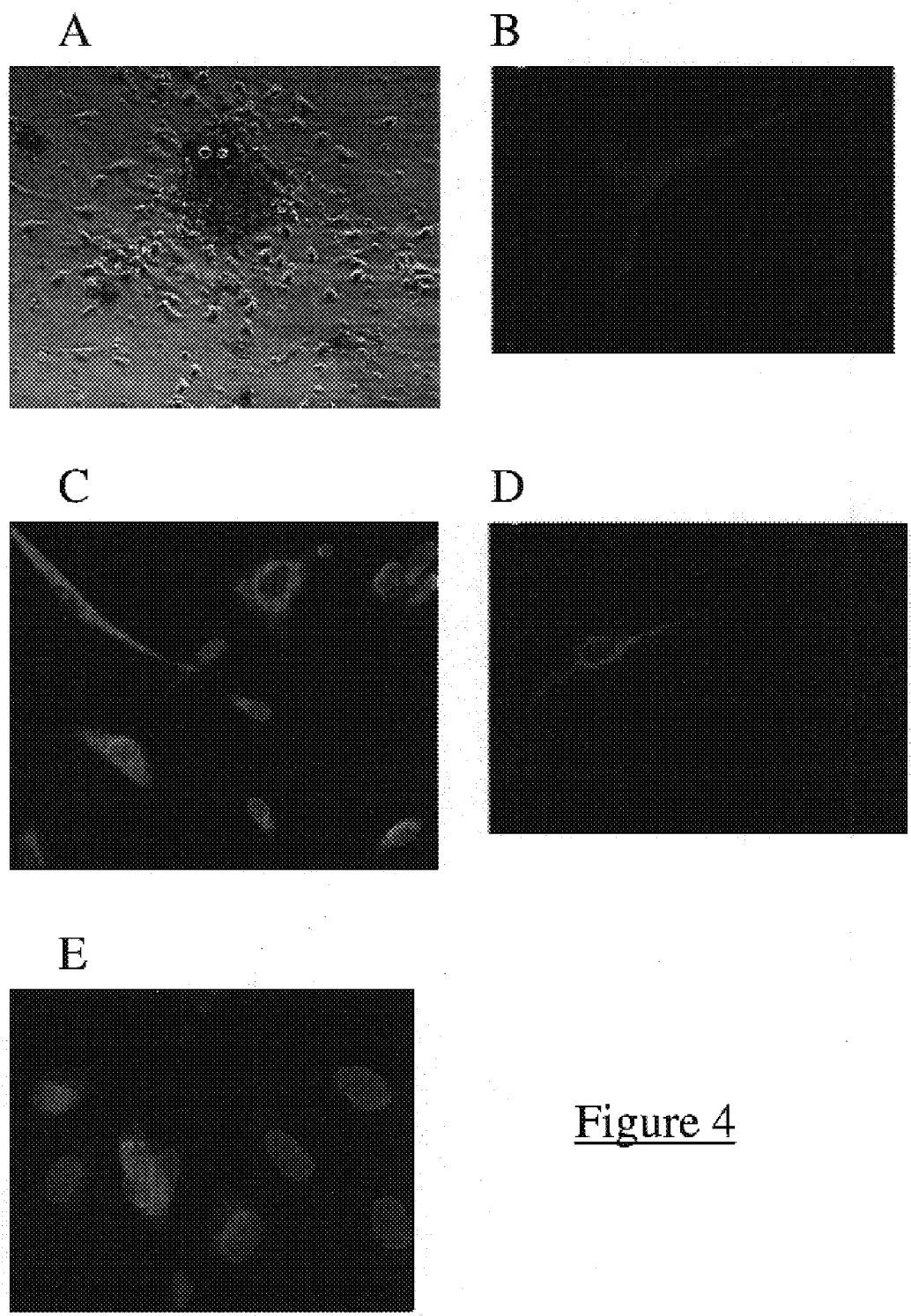
FIG. 4 is executed in color and depicts a differentiation of bone marrow derived cells into neurons and glia in accordance with an embodiment of the present invention. After plating on a substrate in media devoid of growth factors, the bone marrow-derived spheres attached, migrated away from the primary site of attachment, and displayed multiple morphologies, as depicted in FIG. 4A.
Figure 4:
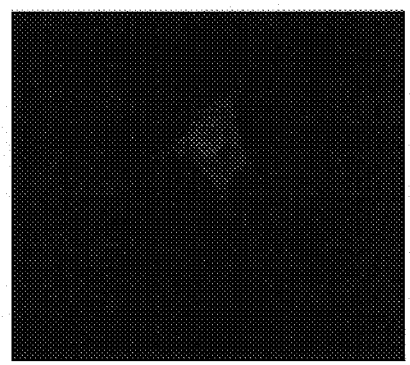
Figure 4:
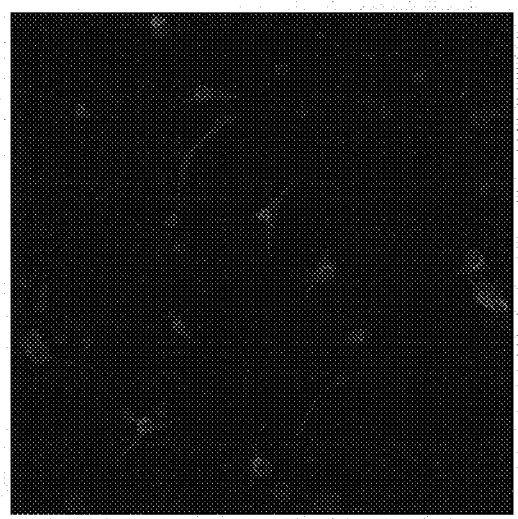
Figure 4:
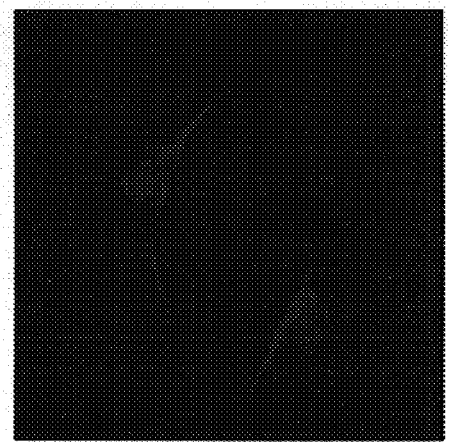

Spheres taken after four days of sub-culture were plated onto laminin-coated 24 well plates in media devoid of growth factors. The spheres attached and cells at the outer margins of each sphere began to develop processes and migrate away from the primary site of attachment (FIG. 1C). Formed spheres detached from the bottom of the plates and thereafter remained free-floating (FIG. 1D); displaying multiple morphologies (FIG. 4A). Neural progenitor cells expressed GFAP (FIGS. 4B and 4C) and the early neuronal marker NeuN (FIGS. 4D and 4E). Scattered cells also expressed the later neuronal marker MAP2 (FIG. 4F). Bone marrow-derived spheres were transplanted into the hippocampus of a syngeneic animal, and cells expressing NeuN were found (FIG. 4G); some of these cells intagrating into the hippocampal structure (FIG. 4H). Data was also collected utilizing alternate antibodies for immunocytochemistry, including CNPase (FIG. 4I) and NF200 (FIGS. 4J and 4K).

Figure 2:
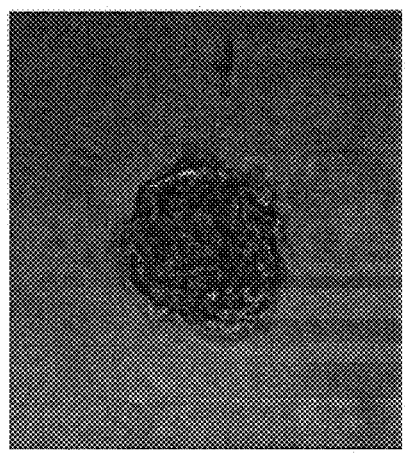
FIG. 2 is executed in color and depicts neural progenitor cells obtained from human bone marrow in accordance with an embodiment of the present invention.
Figure 2:
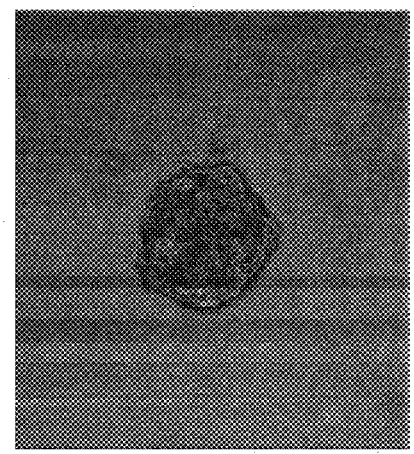
Figure 2:
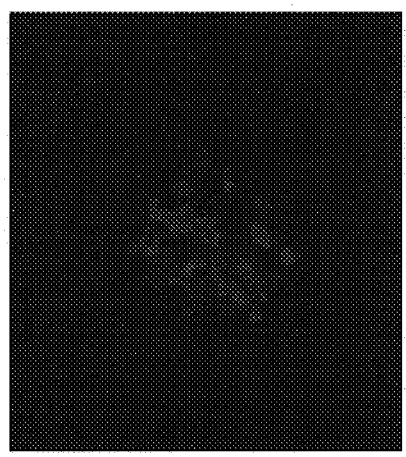
Figure 2:
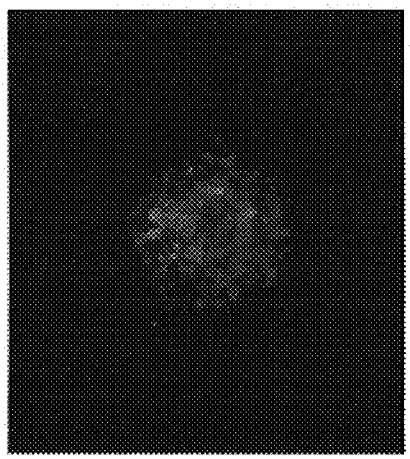
Figure 3:
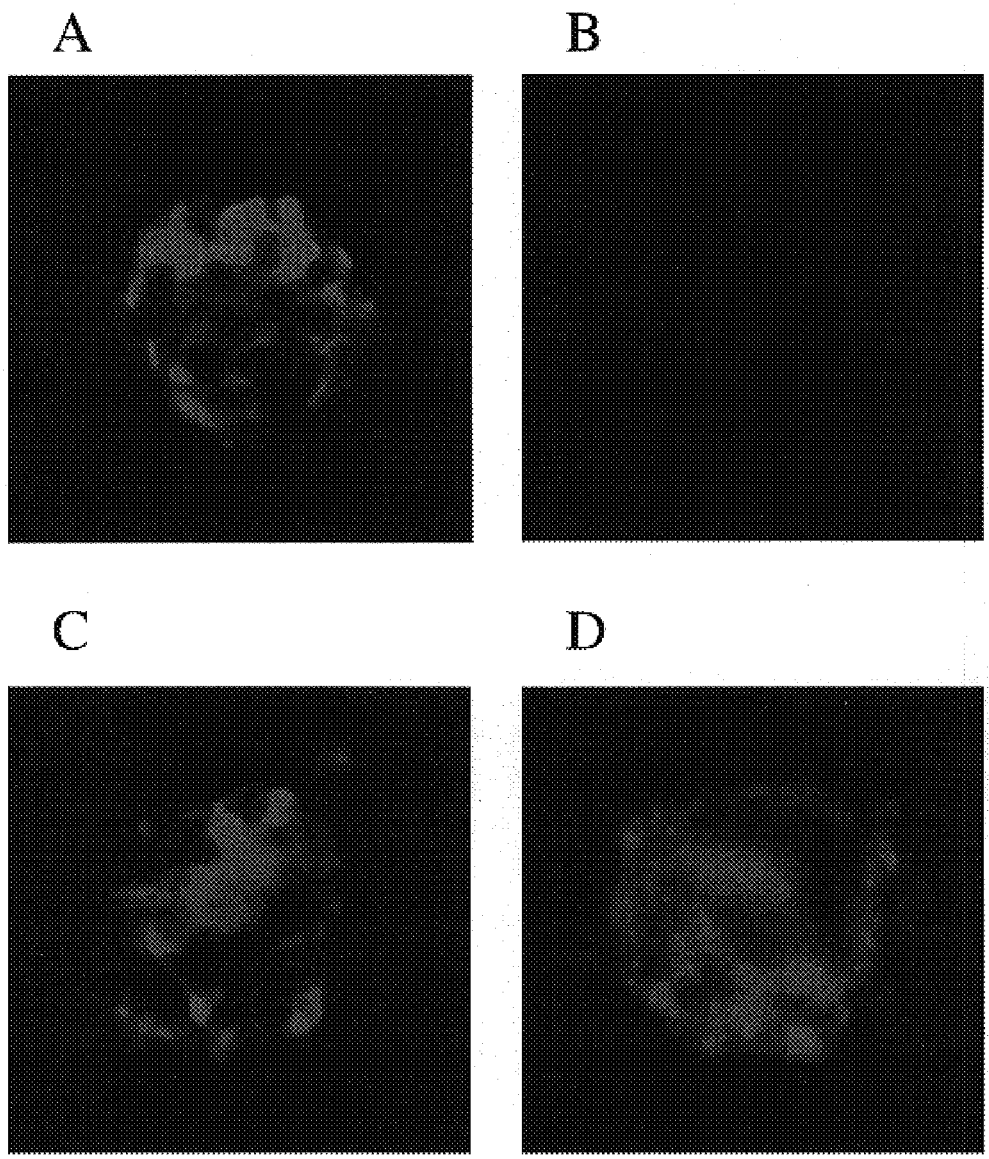
FIG. 3 is executed in color and depicts neural progenitor cells obtained from human bone marrow in accordance with an embodiment of the present invention.

Neurospheres (i.e., cells derived from neural tissue) and bone marrow-derived spheres were morphologically indistinguishable (FIGS. 2A and 2B). The pattern of nestin expression was similar in both (FIGS. 2C and 2D); although bone marrow-derived spheres expressed the ectodermal marker vimentin (FIG. 3A) and also displayed a weak staining for fibronectin (FIG. 3B). Furthermore, the bone marrow-derived spheres exhibited strong expression of CD90 (FIG. 3C), and the majority of cells in spheres also displayed nuclear expression of Neurogenin 1 (FIG. 3D).

Example 2

Gene Transfer into Neural Progenitor Cells Utilizing Replication-Deficient Adenoviral Vectors Type 5 replication-deficient adenoviral vectors bearing either the reporter gene for β-galactosidase or the gene for the cytokine IL-12 were used to infect neural progenitor cells in vitro. 24 hours following infection, successful gene transfer was confirmed using X-gal staining (X-gal Staining Assay Kit available from Gene Therapy Systems, Inc.; San Diego, Calif.) for β-galactosidase-bearing adenoviral-infected progenitor cells, and an IL-12 Enzyme Linked Immunosorbent Assay ("ELISA" kit available from BD Pharmingen; San Diego, Calif.) for IL-12 gene-bearing adenovirus-infected progenitor cells.

Figure 5:
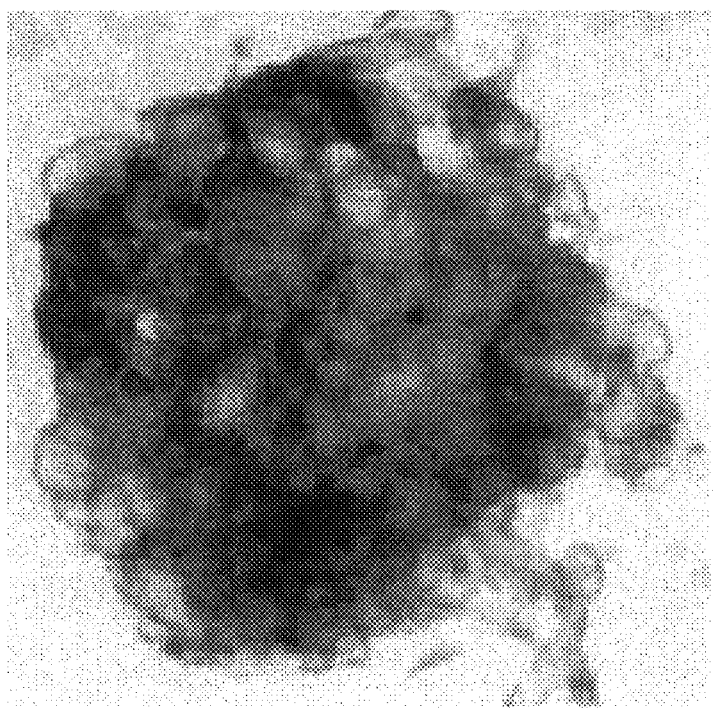
FIG. 5 is executed in color and depicts a gene transfer to neural progenitor cells using a β-galactosidase gene-bearing replication-deficient adenoviral vector in accordance with an embodiment of the present invention.

Successful gene transfer of β-galactosidase was confirmed by positive staining for the X-gal and β-galactosidase-generated blue precipitate in the β-galactosidase-bearing adenovirus-infected progenitor cells (FIG. 5). Successful gene transfer of IL-12 was confirmed by the positive photochromic ELISA reaction in media harvested from the IL-12 gene-bearing adenovirus-infected progenitor cells (Table 1).

TABLE 1

Detection of IL-12 Secretion by ELISA

| | IL-12 Detection by ELISA |
|---|---|
| Cells infected in vitro with AdIL-12 | >> 2 ng/ml |
| Cells infected in vitro with AdLacZ | 4 pg/ml |
| Mock infected cells | Not detected |

Example 3

Figure 6:
FIG. 6 is executed in color and depicts neural progenitor cells infected with green fluorescent protein (GFP) bearing double herpes simplex virus type I in accordance with an embodiment of the present invention.

Gene Transfer into Neural Progenitor Cells Utilizing a Double-Mutated Herpes Simplex Virus Type I A herpes simplex type I virus deleted for the genes encoding the latency activated transcript (LAT) and gamma 34.5 genes (virus denoted DM33) was utilized. The virus contained the gene for GFP under the control of the powerful LAT promoter, and was therefore able to confer constitutive expression of GFP into any successfully infected cell. This vector was used to infect neural progenitor cells in vitro. 72 hours after infection, successful gene transfer was confirmed by viewing GFP expression under a fluorescent light microscope (FIG. 6).

GFP expression was visible in neural progenitor cells 72 hours following infection with DM33. This confirmed the ability to successfully utilize herpes simplex type I for gene transfer to neural progenitor cells.

Example 4

Neural Progenitor Cells Are Capable of Differentiating into Astrocytes, Neurons, and Oligodendroglia Neural progenitor cells were replated in vitro in culture media devoid of essential growth factors and supplemented with retinoic acid (a known stimulator of differentiation). Culture surfaces were coated with poly-D-lysine (available from Sigma) to promote attachment of differentiating cells.

After three to four days, neural progenitor cells had attached to the culture surface and differentiated into astrocytes, neurons, and oligodendroglia. The presence of these cells was specifically confirmed by positive immunocytochemical staining populations for known markers of all three lineages. Specifically, astrocytes in the culture population were positive for GFAP; neurons were positive for β-III tubulin; and oligodendroglia were positive for CNPase. This confirms the multipotency and true progenitor nature of the neural progenitor cells of the present invention.

Example 5

Neural Progenitor Cells Track Spreading Brain Tumor Cells in Vivo

Neural progenitor cells were infected with replication-deficient adenovirus bearing the gene for β-galactosidase as described in Example 2 above. These cells were then transplanted intratumorally into C57bI/6 mice bearing established GL26 brain tumors in their right cerebral hemispheres, respectively. After eleven days, the mice were euthanized, and their brains were immediately harvested, frozen, and sectioned using a cryostat (available from Janis Research Company, Inc.; Wilmington, Mass.). The frozen sections were then stained using an X-gal staining solution to detect the presence of β-galactosidase-expressing neural progenitor cells within the brain tumors.

Neural progenitor cells were clearly visible within the main tumor mass. In addition, neural progenitor cells could clearly be seen tracking pockets of tumor cells that were migrating away from the main tumor mass. This clearly demonstrated the ability of neural progenitor cells to actively follow pockets of tumor cells that disseminate through the brain.

Example 6

Neural Progenitor Cells Track Ischemic Brain Injury in Vivo

The middle cerebral artery of Wistar rats was occluded with a thread embolus for two hours. A drop in perfusion pressure verified effectiveness of occlusion. Neural progenitor cells were infected with replication-deficient adenovirus bearing the gene for β-galactosidase as described in Example 2 above. The cells were infused intracranially either immediately or two hours following middle cerebral artery occlusion. After 48 hours, the rats were euthanized, and their brains were immediately harvested, frozen, and sectioned. The fresh frozen sections were then stained using an X-gal staining solution to detect the presence of β-galactosidase-expressing neural progenitor cells in the brain.

Figure 8:
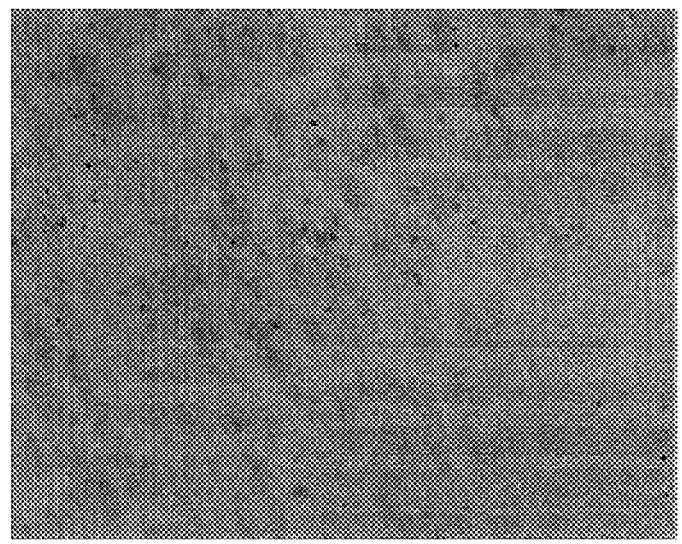
FIG. 8 is executed in color and depicts an intra-arterial delivery of neural progenitor cells into an experimentally induced ischemic lesion in accordance with an embodiment of the present invention. Single cells are distributed widely throughout the brain tissue (FIG. 8A). Transplanted cells exhibit tropism for injured basal ganglia (FIG. 8B; at 400× magnification).
Figure 8:
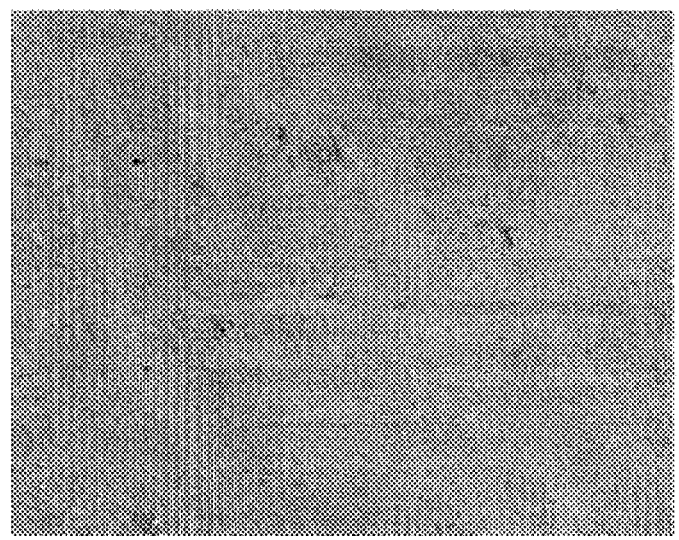

Neural progenitor cells were clearly identifiable in the sectioned brains indicating that these cells can readily cross the blood brain barrier. The transplanted cells were distributed throughout the ischemic part of the brain, mostly as single cells infiltrating the pathological tissue (FIG. 8). While not wishing to be bound by any theory, it is believed that this may be part of the cells' response to chemotactic stimuli originating from the damaged tissue. The cells could also be found in normal parts of the brain and some cells were located in the meninges.

Example 7

Neural Progenitor Cells May Be Generated from Fetal Brain Tissue

Figure 7:
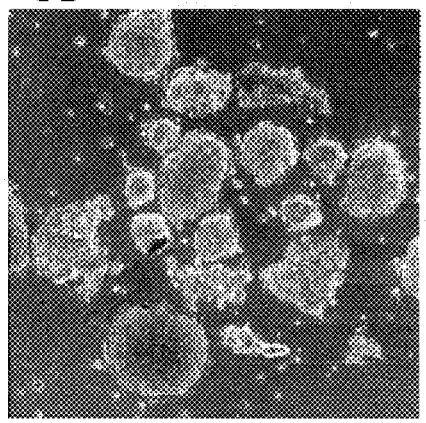
FIG. 7 is executed in color and depicts neurospheres generated from primary fetal brain culture in accordance with an embodiment of the present invention.
Figure 7:
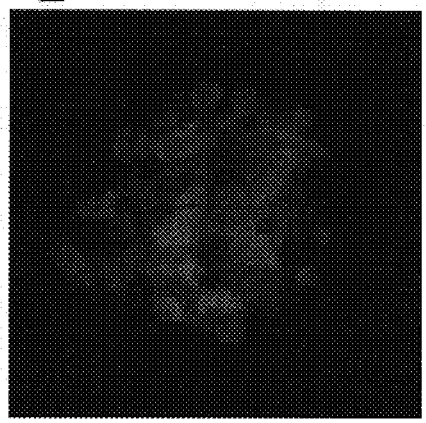
Figure 7:
Figure 7:
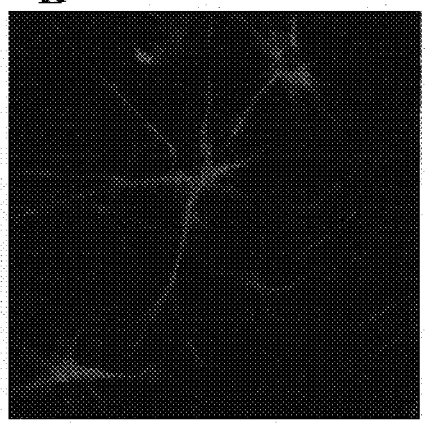
Figure 7:
Figure 7:
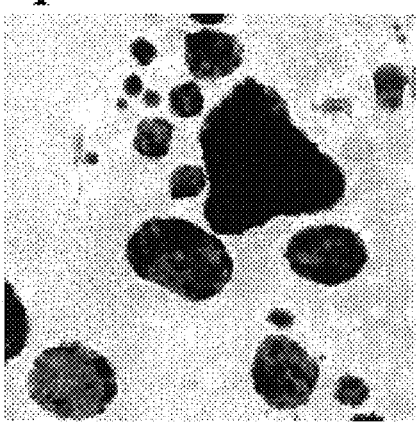

Neurospheres were generated from primary fetal brain culture, in a manner similar to that described with respect to bone marrow in Example 1, above (i.e., cells were cultured in serum-free DMEM/F-12 medium supplemented with B27, 20 ng/ml FGF-2 and 20 ng/ml EGF, along with penicillin and streptomycin). Neural stem cells grew into spherical aggregates 2–3 days following harvest and cultured in growth factor-supplemented media (FIG. 7A). These neurospheres were comprised of neural progenitor cells expressing nestin (FIG. 7B).

The neural stem cells were re-plated in modified culture conditions, after the cells were induced to differentiate. Neurons expressed β-III tubulin (FIG. 7C), astrocytes expressed GFAP (FIG. 7D), and oligodendrocytes expressed CNPase (FIG. 7E). Neural stem cells infected in vitro with AdLacZ expressed β-galactosidase (FIG. 7F).

Example 8

Neural Progenitor Cells Track Tumor Cells in Vivo

Figure 9:
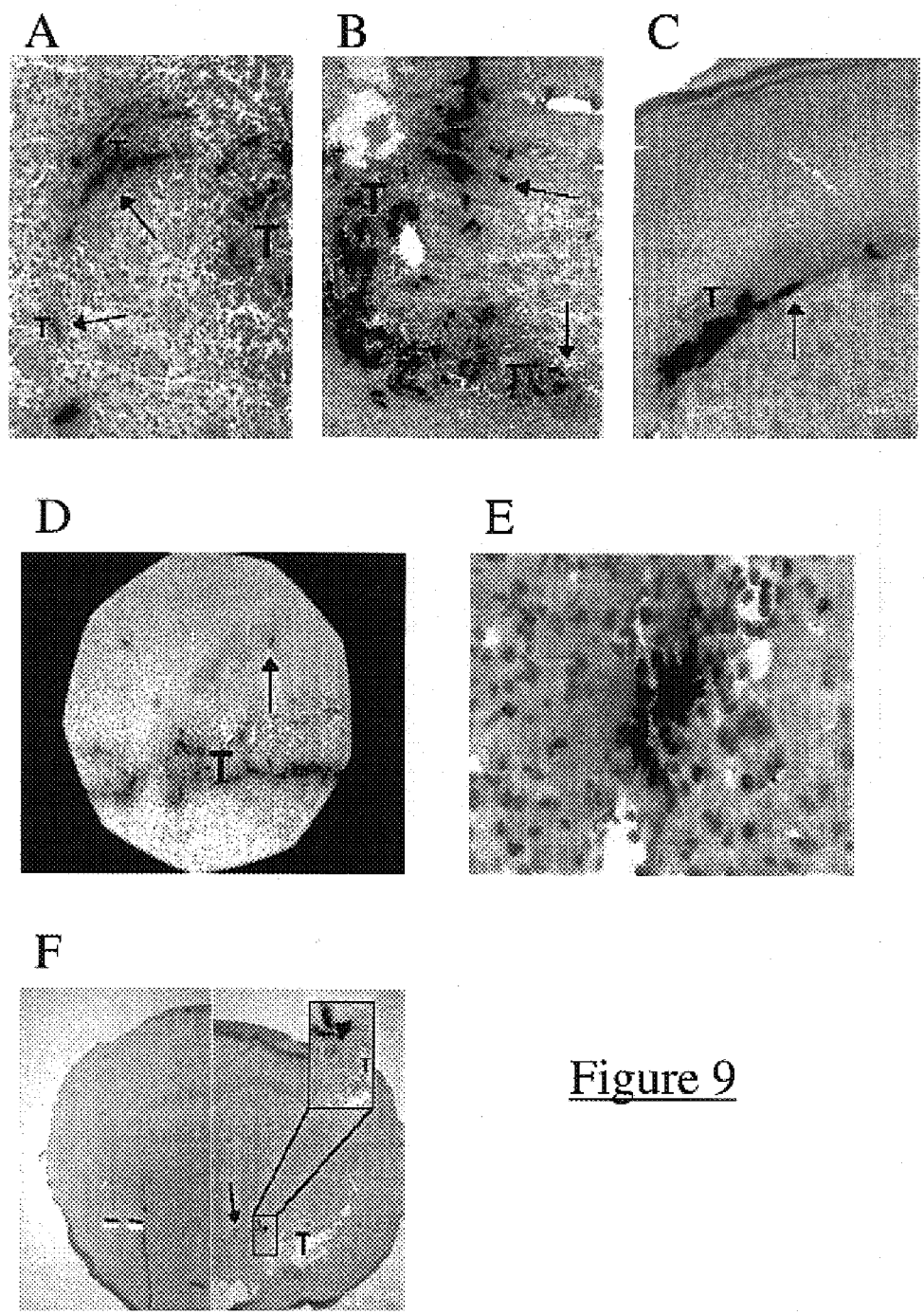
FIG. 9 is executed in color and depicts neural progenitor cells tracking tumor cells in vivo in accordance with an embodiment of the present invention.

Tumors from glioma-bearing mice inoculated with neural progenitor cell-LacZ were stained with X-gal and counterstained with Neutral red. Four distinct patterns of tumor spread were detected and neural progenitor cells were found tracking migrating glioma in each case: (1) a thin outgrowth of tumor cells deep into adjacent normal brain; (2) a direct extension of tumor mass into adjacent tissue; (3) a migration of glioma cells away from the primary tumor bed along a white matter tract; and (4) a tumor microsatellite independent of a main tumor mass (FIGS. 9A–9D, respectively). Interspersed with the tumor cells depicted in the tumor microsatellite (FIG. 9D) were β-galactosidase positive neural progenitor cells; revealed with a high power photomicrograph (FIG. 9E).

Neural progenitor cells were inoculated into a cerebral hemisphere contralateral to an existing tumor. The progenitor cells were introduced into the left cerebral hemisphere (FIG. 9F, left panel), but demonstrated specific, non-random migration into the vicinity of the tumor in the opposite hemisphere (FIG. 9F, right panel and inset box). Neural progenitor cells appear blue (indicating expression of β-galactosidase), whereas tumor cells appear red (hypercellular areas were stained intensively with neural red). Thus, neural progenitor cells display strong tropism for disseminating glioma in vivo.

Example 9

Neural Progenitor Cells Transfected with Cytokines Induce Localized Immune Response in Vivo Neural progenitor cells were transfected with genes that induced them to secrete either IL-12, 3T3-IL-12 or LacZ, as described in Example 2, above. These neural progenitor cells were inoculated into the glioma-bearing brains of rats.

Figure 10:
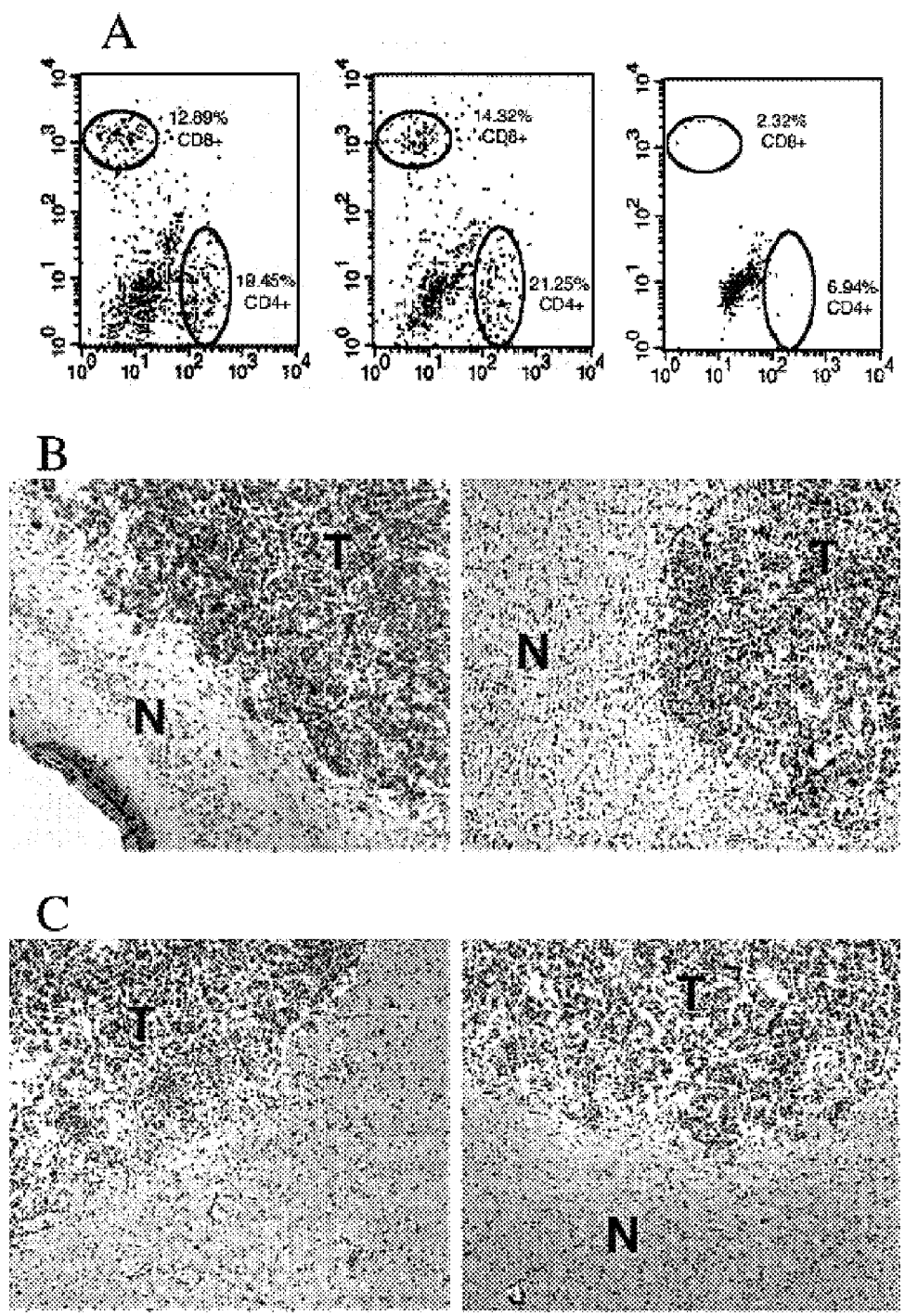
FIG. 10 is executed in color and depicts intratumoral CD4+ and CD8+ T-cell infiltration in accordance with an embodiment of the present invention.
Figure 10:
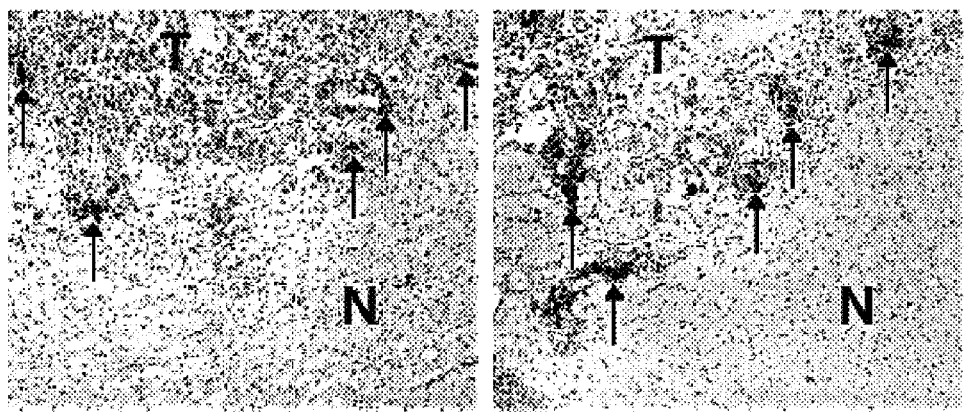
Figure 10:
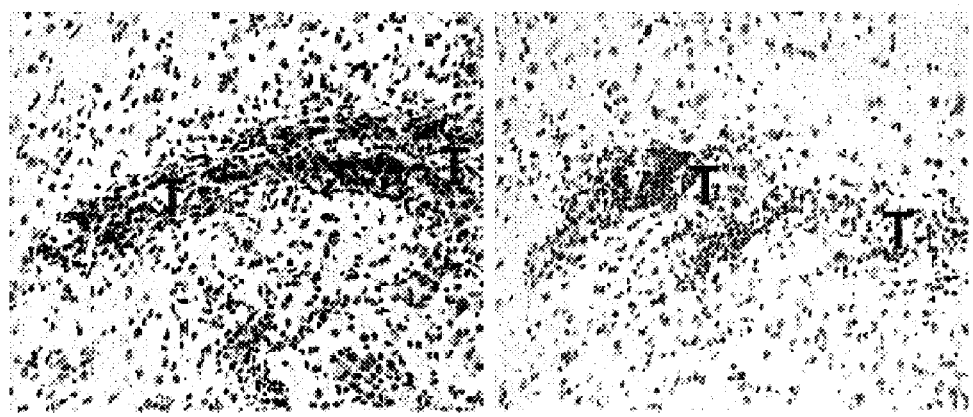
Figure 11:
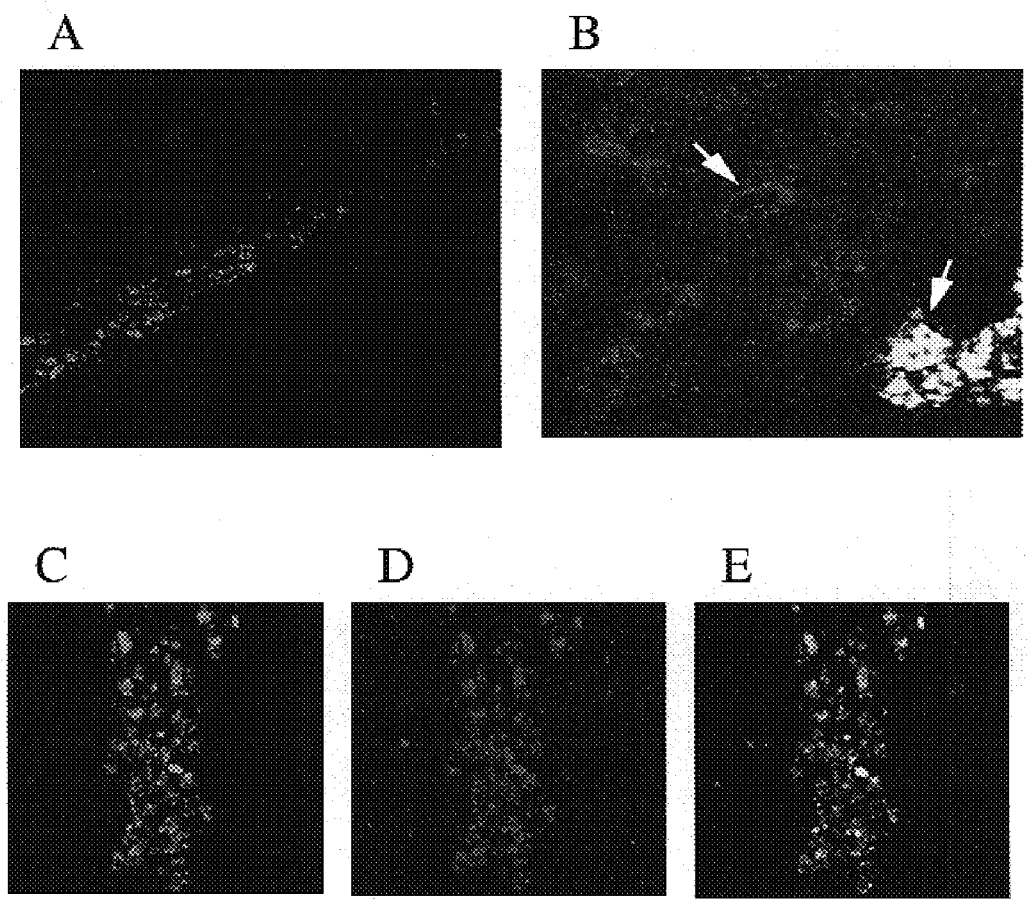
FIG. 11 is executed in color and depicts transplantation of neural progenitor cells expressing GFP into rat hippocampus in accordance with an embodiment of the present invention.

A flow cytometry analysis indicated robust intratumoral T-cell infiltration in brains inoculated with neural progenitor cells secreting IL-12 and 3T3-IL-12 (FIG. 10A, left and center panels, respectively). However, intratumoral T-cell content of brains inoculated with neural progenitor cells secreting LacZ was much lower (FIG. 10A, right panel) and was comparable to infiltration seen in mock-transfected neural progenitor cells and saline-inoculated gliomas (data not shown).

Tumors treated with neural progenitor cells secreting IL-12 demonstrated robust CD4+ and CD8+ T-cell infiltration (FIG. 10D, left and right panels, respectively), with numerous aggregates along the tumor/normal tissue boundary (FIG. 10D). Tumors treated with neural progenitor cells secreting 3T3-IL-12 also demonstrated CD4+ and CD8+ T-cell infiltration (FIG. 10B, left and right panels, respectively), with positive cells interspersed in tumor tissue. However, tumors treated with neural progenitor cells secreting LacZ displayed negligible infiltration of tumors by CD4+ or CD8+ T-cells (FIG. 10C, left and right panels, respectively).

In a comparative analysis of T-cell infiltration in comparable outgrowths from a primary tumor bed, tumor microsatellites in brains treated with neural progenitor cells secreting IL-12 demonstrated robust T-cell infiltration, whereas those in brains treated with neural progenitor cells secreting 3T3-IL-12 did not (FIG. 10E, left and right panels, respectively).

Example 10

Figure 12:
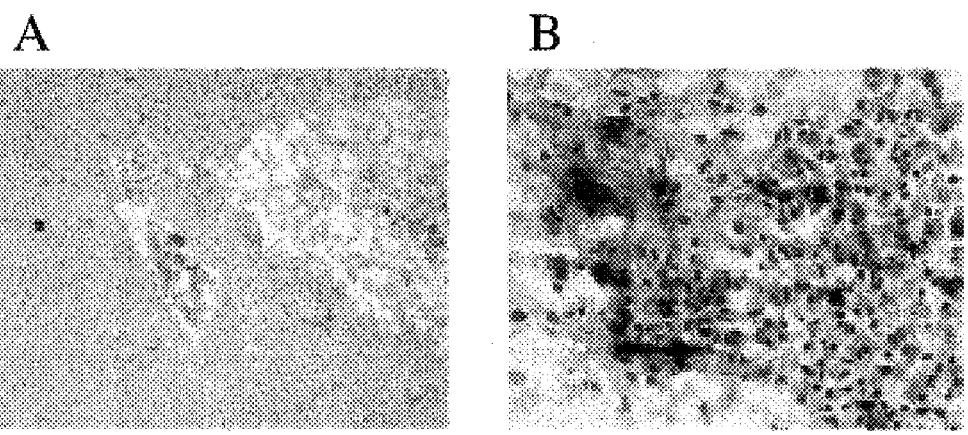
FIG. 12 is executed in color and depicts neural progenitor cells, stained for LacZ, seen in the tumor outgrowth migrating out from the main tumor mass at 10× (FIG. 12A) and 40× (FIG. 12B) magnification. The sections were counterstained with hematoxylin.

Neural Progenitor Cells Transfected with β-Galactosidase Track Tumor Cells in Vivo RG2 tumor cells (100,000 in 5 ul of media) were stereotactically implanted into the striatum of Wistar rats. Two days following tumor implantation, 30,000 bone marrow derived cells infected with adenovirus carrying the β-galactosidase gene were implanted into the same site. The immunohistological analysis was done 60 days following cell implantation. As depicted in FIG. 12, the cells, stained for LacZ, can be seen in the tumor outgrowth migrating out from the main tumor mass at 10× (FIG. 12A) and 40× (FIG. 12B) magnification. The sections were counterstained with hematoxylin.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims, rather than the foregoing description, and all changes that come within the meaning and range of equivalency of the claims are therefore intended to be embraced therein.

What is claimed is:

1. A method to generate neural progenitor cells, the method comprising:
   culturing whole bone marrow from a mammal in a medium comprising fibroblast growth factor-2 (FGF-2) and epidermal growth factor (EGF) to produce a neural progenitor cells.

2. The method of claim 1, wherein the whole bone marrow is obtained from an adult mammal.

3. The method of claim 1, wherein the whole bone marrow is obtained from a fetus.

4. The method of claim 1, wherein the medium is Dulbecco's modified Eagle medium (DMEM).

5. The method of claim 1, wherein the medium further comprises a supplement.

6. The method of claim 5, wherein the supplement is selected from the group consisting of B27, N2, and combinations thereof.

7. The method of claim 1, wherein the medium further comprises an additional compound selected from the group consisting of interleukin-3 (IL-3), stem cell factor-1 (SCF-1), sonic hedgehog (Shh), fms-like tyrosine kinase-3 (Flt3) ligand, leukemia inhibitory factor (LIF), and combinations thereof.

8. The method of claim 1, wherein the medium further comprises an antibiotic.

9. The method of claim 8, wherein the antibiotic is selected from the group consisting of penicillin, streptomycin, and combinations thereof.

10. The method of claim 1, wherein clusters of the neural progenitor cells develop in the medium, and the method further comprises separating at least one cluster from the medium.

11. The method of claim 10, further including subculturing the at least one cluster.

12. The method of claim 11, wherein subculturing the at least one cluster further comprises culturing the at least one cluster in a medium comprising FGF-2 and EGF.

13. A method to generate neural progenitor cells, the method comprising:
   culturing whole bone marrow from a mammal in Dulbecco's modified Eagle Medium (DMEM) comprising B27, penicillin, streptomycin, fibroblast growth factor-2 (FGF-2) and epidermal growth factor (EGF),
   wherein sphere clusters of the neural progenitor cells develop in the medium, and the method further comprises separating at least one sphere cluster from the medium and subculturing the at least one sphere cluster in a medium comprising FGF-2 and EGF to produce neural progenitor cells.

* * * * *